(12) United States Patent
Kitagawa et al.

(10) Patent No.: US 8,323,669 B2
(45) Date of Patent: Dec. 4, 2012

(54) POLYMER CONJUGATE OF TAXANE

(75) Inventors: Masayuki Kitagawa, Kita-ku (JP); Keizou Ishikawa, Kita-ku (JP); Takeshi Onda, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 426 days.

(21) Appl. No.: 12/225,230

(22) PCT Filed: Mar. 22, 2007

(86) PCT No.: PCT/JP2007/055809
§ 371 (c)(1),
(2), (4) Date: Dec. 10, 2008

(87) PCT Pub. No.: WO2007/111211
PCT Pub. Date: Oct. 4, 2007

(65) Prior Publication Data
US 2010/0234537 A1 Sep. 16, 2010

(30) Foreign Application Priority Data
Mar. 28, 2006 (JP) ................ 2006-087176

(51) Int. Cl.
A61K 31/77 (2006.01)
A61K 47/48 (2006.01)
A61P 35/00 (2006.01)

(52) U.S. Cl. .............. 424/400; 424/78.08; 424/78.17; 424/78.19; 424/78.2; 424/78.21; 424/78.22; 424/78.37

(58) Field of Classification Search .......... 424/400, 424/78.08, 78.17, 78.19, 78.2, 78.21, 78.22, 424/78.37
See application file for complete search history.

(56) References Cited

U.S. PATENT DOCUMENTS

| | | | |
|---|---|---|---|
| 3,979,449 A | 9/1976 | Hirsbrunner et al. | |
| 4,734,512 A | 3/1988 | Kaneko et al. | |
| 4,892,733 A | 1/1990 | Bichon et al. | |
| 5,037,883 A | 8/1991 | Kopecek et al. | |
| 5,412,072 A | 5/1995 | Sakurai et al. | |
| 5,438,072 A | 8/1995 | Bobee et al. | |
| 5,552,517 A | 9/1996 | Martin | |
| 5,571,889 A | 11/1996 | Katoh et al. | |
| 5,614,549 A | 3/1997 | Greenwald et al. | |
| 5,639,832 A | 6/1997 | Kroner et al. | |
| 5,877,205 A | 3/1999 | Andersson | 514/449 |
| 6,025,385 A | 2/2000 | Shimizu et al. | |
| 6,153,655 A | 11/2000 | Martinez et al. | |
| 6,262,107 B1* | 7/2001 | Li et al. | 514/449 |
| 6,322,817 B1 | 11/2001 | Maitra et al. | |
| 6,376,470 B1 | 4/2002 | Greenwald et al. | |
| 6,410,731 B2 | 6/2002 | Curran et al. | |
| 6,458,347 B1 | 10/2002 | Sugawara et al. | |
| 6,596,757 B1 | 7/2003 | Chari et al. | 514/449 |
| 6,713,454 B1 | 3/2004 | Ekwuribe et al. | |
| 6,720,306 B2 | 4/2004 | Greenwald et al. | |
| 7,138,490 B2 | 11/2006 | Nakanishi et al. | |
| 7,495,099 B2 | 2/2009 | Kitagawa et al. | |
| 7,700,709 B2 | 4/2010 | Masuda et al. | |
| 7,820,759 B2 | 10/2010 | Shimizu et al. | |
| 8,188,222 B2 | 5/2012 | Yamamoto et al. | |
| 2001/0003779 A1 | 6/2001 | Curran et al. | |
| 2001/0014354 A1 | 8/2001 | Yokoyama et al. | |
| 2001/0041189 A1 | 11/2001 | Xu | |
| 2002/0016285 A1 | 2/2002 | Bhatt et al. | |
| 2002/0099013 A1 | 7/2002 | Piccariello et al. | |
| 2002/0119951 A1 | 8/2002 | Seyedi et al. | |
| 2002/0161062 A1 | 10/2002 | Biermann et al. | |
| 2002/0183259 A1 | 12/2002 | Choe et al. | |
| 2003/0032593 A1 | 2/2003 | Wender et al. | |
| 2003/0054977 A1 | 3/2003 | Kumar et al. | |
| 2003/0149003 A1 | 8/2003 | Chaplin et al. | |
| 2005/0119193 A1 | 6/2005 | Motoyama | |
| 2005/0147617 A1 | 7/2005 | Ji et al. | |
| 2006/0057219 A1 | 3/2006 | Nagasaki et al. | |
| 2006/0067910 A1 | 3/2006 | Kitagawa et al. | |
| 2006/0099265 A1* | 5/2006 | Shimizu et al. | 424/486 |
| 2006/0233883 A1 | 10/2006 | Ishihara et al. | |
| 2007/0004674 A1 | 1/2007 | Shiotsu et al. | |
| 2007/0196497 A1 | 8/2007 | Pouliquen et al. | |
| 2008/0113028 A1 | 5/2008 | Shimizu et al. | |
| 2008/0145432 A1 | 6/2008 | Kakizawa et al. | |
| 2008/0221062 A1 | 9/2008 | Miyamoto et al. | |

(Continued)

FOREIGN PATENT DOCUMENTS
CA 2 383 240 A1 3/2001
(Continued)

OTHER PUBLICATIONS

Chinese communication dated Aug. 11, 2010 in a co-pending foreign application (CN2007800177809).
Journal of Peptide Science, vol. 3, 141-144 (1997); Jan Izdebski et al.; "Evaluation of Carbodiimides Using a Competition Method".
International Search Report dated May 15, 2007.
Chinese Office Action dated Nov. 10, 2010 in co-pending U.S. Appl. No. 12/309,061, filed Mar. 3, 2009 Foreign Application No. 200780027210.8.
Korean Office Action dated Nov. 8, 2010 in co-pending U.S. Appl. No. 10/548,998, filed Oct. 31, 2005 Foreign Application No. 10-2005-7017245.
Bioorganic & Medicinal Chemistry Letters 15 (2005) pp. 3338-3343, "The identification, synthesis, protein crystal structure and in vitro biochemical evaluation of a new 3,4-diarylpyrazole class of Hsp90 inhibitors", Cheung, et al.

(Continued)

Primary Examiner — Ana Woodward
(74) Attorney, Agent, or Firm — Nields, Lemack & Frame, LLC

(57) ABSTRACT

[Problems] To provide a novel taxane derivative which can release the medicinal substance in a bioenzyme-independent manner, is expected to have an effective therapeutic efficacy, and has a water-solubility.
[Means for Solving Problems] Disclosed is a polymer conjugate of a taxane, which comprises a polymer having a polyethylene glycol moiety and two or more succinic acid monoamide moieties and a taxane, wherein a carboxylate group in the polymer and an alcoholic hydroxyl group in the taxane are bound to each other via an ester bonding.

6 Claims, 1 Drawing Sheet

U.S. PATENT DOCUMENTS

| | | |
|---|---|---|
| 2008/0269218 A1 | 10/2008 | Kuramochi et al. |
| 2008/0280937 A1 | 11/2008 | Leamon et al. |
| 2009/0012252 A1 | 1/2009 | Masuda et al. |
| 2009/0162313 A1 | 6/2009 | Kitagawa et al. |
| 2009/0239782 A1 | 9/2009 | Nakamura et al. |
| 2009/0275732 A1 | 11/2009 | Hirotsu et al. |
| 2009/0281300 A1 | 11/2009 | Yamamoto et al. |
| 2010/0004403 A1 | 1/2010 | Kitagawa et al. |
| 2010/0029849 A1 | 2/2010 | Yamamoto et al. |
| 2010/0234537 A1 | 9/2010 | Kitagawa et al. |
| 2010/0292414 A1 | 11/2010 | Kitagawa et al. |
| 2011/0201754 A1 | 8/2011 | Kitagawa |
| 2011/0294980 A1 | 12/2011 | Nakanishi et al. |
| 2012/0116051 A1 | 5/2012 | Kitagawa et al. |

FOREIGN PATENT DOCUMENTS

| | | |
|---|---|---|
| CA | 2 334 615 A1 | 8/2001 |
| CN | 1307866 A | 8/2001 |
| CN | 1708540 A | 12/2005 |
| EP | 0 397 307 A2 | 11/1990 |
| EP | 0 583 955 A2 | 2/1994 |
| EP | 0 757 049 A1 | 2/1997 |
| EP | 1 127 570 A2 | 8/2001 |
| EP | 1 857 446 A1 | 11/2007 |
| JP | 61-243026 A | 10/1986 |
| JP | 62-96088 A | 5/1987 |
| JP | 62-145093 A | 6/1987 |
| JP | 63-10789 A | 1/1988 |
| JP | 63-23884 A | 2/1988 |
| JP | 63-502037 A | 8/1988 |
| JP | 64-61422 A | 3/1989 |
| JP | 64-61423 A | 3/1989 |
| JP | 2-300133 A | 12/1990 |
| JP | 5-955 A | 1/1993 |
| JP | 5-117385 A | 5/1993 |
| JP | 6-107565 A | 4/1994 |
| JP | 6-206815 A | 7/1994 |
| JP | 6-206830 A | 7/1994 |
| JP | 6-206832 | 7/1994 |
| JP | 6-296088 A | 10/1994 |
| JP | 6-310789 A | 11/1994 |
| JP | 6-323884 A | 11/1994 |
| JP | 8-48766 A | 2/1996 |
| JP | 8-503689 | 4/1996 |
| JP | 8-507558 A | 8/1996 |
| JP | 8-310970 | 11/1996 |
| JP | 8-310970 A | 11/1996 |
| JP | 2694923 A | 9/1997 |
| JP | 10-513187 | 12/1998 |
| JP | 11-335267 A | 12/1999 |
| JP | 2000-515132 | 11/2000 |
| JP | 2000-516948 A | 12/2000 |
| JP | 2000-517304 A | 12/2000 |
| JP | 2001-226294 A | 8/2001 |
| JP | 3268913 A | 1/2002 |
| JP | 2002-69184 A | 3/2002 |
| JP | 2002-508400 A | 3/2002 |
| JP | 2002-512265 A | 4/2002 |
| JP | 3310000 A | 5/2002 |
| JP | 2003-509385 A | 3/2003 |
| JP | 2003-509386 | 3/2003 |
| JP | 2003-511349 A | 3/2003 |
| JP | 2003-511423 | 3/2003 |
| JP | 2003-524028 A | 8/2003 |
| JP | 2003-525238 A | 8/2003 |
| JP | 2003-527443 A | 9/2003 |
| JP | 2003-342167 A | 12/2003 |
| JP | 2003-342168 A | 12/2003 |
| JP | 2003-342269 | 12/2003 |
| JP | 2004-39869 A | 2/2004 |
| JP | 2004-530736 A | 10/2004 |
| JP | 2004-532289 A | 10/2004 |
| JP | 2005-51922 A | 2/2005 |
| JP | 2005-507912 A | 3/2005 |
| JP | 2005-508832 A | 4/2005 |
| JP | 2005-517675 A | 6/2005 |
| JP | 2005-519122 A | 6/2005 |
| JP | 2005-533026 | 11/2005 |
| JP | 2006-510627 A | 3/2006 |
| JP | 2006-511571 A | 4/2006 |
| JP | 2006-120914 A | 5/2006 |
| JP | 2006-517572 A | 7/2006 |
| JP | 2006-521367 A | 9/2006 |
| JP | 2006-524673 A | 11/2006 |
| JP | 2007-111211 A | 5/2007 |
| JP | 2007-511586 A | 5/2007 |
| JP | 2008-41610 A | 2/2008 |
| WO | 93/24476 | 12/1993 |
| WO | 96/23794 A | 8/1996 |
| WO | 97/38727 | 10/1997 |
| WO | 98/02426 | 1/1998 |
| WO | 98/07713 A | 2/1998 |
| WO | 98/08489 A1 | 3/1998 |
| WO | 99/53951 A | 10/1999 |
| WO | 01/19361 A2 | 3/2001 |
| WO | 01/19406 A2 | 3/2001 |
| WO | 01/19407 A2 | 3/2001 |
| WO | 01/26693 A2 | 4/2001 |
| WO | 01/64198 A2 | 9/2001 |
| WO | 01/70275 A2 | 9/2001 |
| WO | 01/92584 A1 | 12/2001 |
| WO | 02/06279 A1 | 1/2002 |
| WO | 02/065986 A2 | 8/2002 |
| WO | 02/065988 A2 | 8/2002 |
| WO | 02/066066 A1 | 8/2002 |
| WO | 03/000771 A1 | 1/2003 |
| WO | 03/035008 A2 | 5/2003 |
| WO | 03/055860 A1 | 7/2003 |
| WO | 2004/039869 | 5/2004 |
| WO | 2004/050087 A1 | 6/2004 |
| WO | 2004/056782 A1 | 7/2004 |
| WO | 2004/072051 A1 | 8/2004 |
| WO | 2004/082718 A1 | 9/2004 |
| WO | 2004/096212 A1 | 11/2004 |
| WO | 2005/000300 A1 | 1/2005 |
| WO | 2005/018674 A1 | 3/2005 |
| WO | 2005/066214 A1 | 7/2005 |
| WO | 2006/055760 A1 | 5/2006 |
| WO | 2006/095668 A1 | 9/2006 |
| WO | 2006/095783 A1 | 9/2006 |
| WO | 2006/115293 A1 | 11/2006 |
| WO | 2006/120914 A | 11/2006 |
| WO | 2006/120915 A1 | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |

OTHER PUBLICATIONS

Molecular Cancer Therapeutics, 2006, 5(6), Jun. 2006, pp. 1628-1637, "Preclinical pharmacokinetics and metabolism of a novel diaryl pyrazole resorcinol series of heat shock protein 90 inhibitors", Smith, et al.

Registry Entry for Registry No. 171009-07-7, which entered STN on Dec. 6, 1995, 3 pages.

Registry Entry for Registry No. 7689-03-4, which entered STN on Nov. 16, 1984, 3 pages.

Merriam-Webster Online Dictionary entry for "Derivative", (http://www.merriam-webster.com/dictionary/derivative), last accessed Feb. 9, 2011, 3 pages.

International Search Report dated Dec. 24, 2003 in U.S. patent 7,495,099.

Taiwanese communication dated Nov. 30, 2006 in U.S. patent 7,495,099.

Russian communication dated Apr. 20, 2007 in U.S. patent 7,495,099.

European communication dated Sep. 25, 2008 in U.S. patent 7,495,099.

International Search Report dated May 11, 2004 in co-pending U.S. Appl. No. 10/548,998.

Chinese communication dated Oct. 20, 2006 in co-pending U.S. Appl. No. 10/548,998.
Russian communication dated Jun. 27, 2007 in co-pending U.S. Appl. No. 10/548,998.
European communication dated Feb. 17, 2009 in co-pending U.S. Appl. No. 10/548,998.
Chinese communication dated Apr. 17, 2009 in co-pending U.S. Appl. No. 10/548,998.
European communication dated Jun. 5, 2009 in co-pending U.S. Appl. No. 10/548,998.
International Search Report dated Nov. 15, 2005 in co-pending U.S. Appl. No. 12/322,322.
International Search Report dated Jul. 25, 2006 in U.S. Patent 7,700,709.
International Search Report dated Aug. 21, 2007 in co-pending U.S. Appl. No. 12/226,962.
European communication dated Oct. 23, 2009 in co-pending U.S. Appl. No. 12/226,962.
International Search Report dated Oct. 16, 2007 in co-pending U.S. Appl. No. 12/309,061.
International Search Report dated Jan. 8, 2008 in co-pending U.S. Appl. No. 12/311,086.
International Search Report dated Jan. 29, 2008 in co-pending U.S. Appl. No. 12/312,009.
A.V. Shur, "High-Molecular Weight Compounds"; Course for Universities, Third Edition, Revised and supplemented, "Visshaja Shkola" Publishing House, 1981, 656 pages, see p. 265).
Chemical Abstracts, 6001, vol. 132; Oct. 10, 2000 No. 2-XP-002168038.
Merriam-Webster's Collegiate Dictionary—Eleventh Edition 2004.
J. Org. Chem. 2001, 66, 8135-8138; Keirs Gaukroger, et al.; "Novel Synthesis of Cis and Trans Isomers of Combretastatin A-4".
Anti-Cancer Drug Design; vol. 14, No. 6, Dec. 1999—ISSN 0266-9536.
Journal of Pharmaceutical Sciences, vol. 92, No. 7, Jul. 2003; Monica L. Adams et al.; "MiniReview—Amphiphilic Block Copolymers for Drug Delivery".
Chemistry and Biology, vol. 11, 787-797, Jun. 2004; Maria Vilenchick et al.; "Targeting Wide-Range Oncogenic Transformation via PU24FCl, a specific Inhibitor of Tumor Hsp90".
Trends in Molecular Medicine vol. 8, No. 4 (Suppl.) 2002; Len Neckers; "Hsp90 inhibitors as novel cancer chemotherapeutic agents".
Current Cancer Drug Targets, 2003, 3, 385-390; Udai Banerji et al.; "The Clinical Applications of Heat Shock Protein Inhibitors in Cancer Present and Future".
Cancer Sci; Feb. 2004; vol. 95; No. 2; 105-111; Akira Matsuda et al.; "Antitumor Activity of Sugar-Modified Cytosine Nucleosides".
Cancer Research 44, 25-30, Jan. 1984; Yoshinori Kato et al.; "Antitumor Activity of 1-B-D-Arabinofuranosylcytosine Conjugated with Polyglutamic Acid and Its Derivative".
Journal of Controlled Release 79 (2002) 55-70; Yun H. Choe et al.; "Anticancer Drug Delivery Systems: Multi-Loaded N4-acyl poly-(ethylene glycol) prodrugs of ara-C. II. Efficacy in ascites and solid tumors".
Journal of Pharmacokinetics and Biopharmaceutics, vol. 23, No. 4, 1995; Claudia S. Leopold; In vivo Pharmacokinetic Study for the Assessment of Poly(L-Aspartic Acid) as a Drug Carrier for Colon-Specific Drug Delivery).
International Search Report dated Dec. 9, 2008 in co-pending U.S. Appl. No. 12/678,620.
Advanced Drug Delivery Reviews 20 (1996) 1995-201; K. Yokoyama et al; "Limethason as a lipid microsphere preparation: An overview".
International Search Report dated Jan. 29, 2008 in co-pending U.S. Appl. No. 12/312,157.
Colloids and Surfaces B: Biointerfaces V. 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000), pp. 607-611, "Methotrexate Esters of Poly (EthyleneOxide)-Block-Poly (2-Hydroxyethyl-L-Aspartamide). Part I: Effects of the Level of Methotrexate Conjugation on the Stability of Micelles and on Drug Release", Li, et al.
International Search Report dated Jul. 21, 2009 in co-pending international patent application No. PCT/JP2009/058325.
Taiwan Communication, with English translation, dated Jul. 22, 2011 in co-pending Taiwan Patent Application No. 094132581.
Taiwanese Communication, with English translation, dated Dec. 14, 2011 in co-pending Taiwanese Application No. 094132581.
International Search Report dated Aug. 10, 2010 in co-pending PCT application No. PCT/JP2010/058034.
Chinese Communication, with English translation, dated Sep. 23, 2011 in co-pending Chinese patent application No. 2007800177809.
Journal of Controlled Release, 2001, V. 74, No. 1-3, pp. 295-302, paragraph of "2. Structure of NK911", "Development of the polymer micelle carrier system for doxorubicin", Nakanishi, et al.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
Chinese Communication, with English translation, dated Oct. 10, 2011 in co-pending Chinese Patent Application No. 200880109404.7.
European Communication, dated Oct. 28, 2011 in co-pending European Patent Application No. EP 05783310.5.
Australian Communication, dated Oct. 28, 2011 in co-pending Australian Patent Application No. 2007252678.
Russian Communication, with English translation, dated May 16, 2011 in co-pending foreign patent application No. RU 2008149932/04.
European Communication mailed Jan. 27, 2012 in co-pending European Patent Application No. 07831039.8.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.

* cited by examiner

POLYMER CONJUGATE OF TAXANE

TECHNICAL FIELD

The present invention relates to a taxane-polymer conjugate in which a carboxylic acid group of a polymer having a polyethylene glycol moiety and two or more succinic acid monoamide moieties is ester-bonded to an alcoholic hydroxyl group of a taxane, a method for producing the same, and the use of the same.

BACKGROUND ART

Taxanes, represented by paclitaxel, docetaxel and the like, are anti-cancerous alkaloids, mainly contained in plants such as yew trees, or derivatives thereof. In general, the taxanes have an extremely poor solubility in water, and therefore research to impart water-solubility to the taxanes has been conducted.

For example, Patent Document 1 and Patent Document 2 describe polymeric derivatives of paclitaxel bound to polyethylene glycol as a prodrug.

However, in these polymeric derivatives of paclitaxel, only one or two paclitaxel molecules can be bound to one molecule of polyethylene glycol, and as a result, a large amount of the polymer is required for the administration of an effective amount of the drug.

Furthermore, Patent Document 3 describes a derivative in which polyglutamic acid is bound to an alcoholic hydroxyl group of paclitaxel or docetaxel. However, no description is given on a polymeric derivative in which a taxane is bound to a polymer having a polyethylene glycol moiety and two or more succinic acid monoamide moieties.

Patent Document 4 describes a molecule in which a drug is bound to a block copolymer of polyethylene glycol and polyaspartic acid, and the molecule forms micelles and has water solubility. Patent Document 5 describes a polymeric carrier in which a hydrophobic substance is bound to a carboxylic acid group in a side chain of a block copolymer of polyethylene glycol and poly(acidic amino acid), as a carrier functioning as a polymeric drug carrier. Patent Document 6 describes a polymer derivative of camptothecins, in which a carboxylic acid group in a side chain of a block copolymer of polyethylene glycols and polyglutamic acid is bound to a phenolic hydroxyl group of the camptothecins. However, none of Patent Documents 4 to 6 refers to conjugates of taxanes.

Patent Document 1: International Publication No. WO 93/24476 Pamphlet
Patent Document 2: Japanese Patent Application Laid Open (KOKAI) No. 10-513187
Patent Document 3: Japanese Patent Application Laid Open (KOHYO) No. 2003-511423
Patent Document 4: Japanese Patent No. 2694923
Patent Document 5: Japanese Patent No. 3268913
Patent Document 6: International Publication No. WO 2004/39869 Pamphlet

DISCLOSURE OF THE INVENTION

Problems to be Solved by the Invention

A bond between a polyethylene glycol moiety and a drug as described in Patent Document 1 or Patent Document 2 is cleavable by hydrolyzing enzymes in the body, by which the delivery and release of the drug is controlled. However, the hydrolyzing enzymes in the body are believed to vary widely among different species as well as among individuals within the same species. Therefore, there is concern that the effect of the released drug would be greatly different among individuals when the cleavage of bonds to the drug depends on the hydrolyzing enzymes.

Similarly, the drug is released from the paclitaxel derivative in which the drug is bound to polyglutamic acid described in the Patent Document 3 by hydrolysis depending on the hydrolyzing enzymes, and therefore the individual difference in drug efficacy would be concerned.

In the case of the adriamycin conjugate described in the Patent Document 4 in which a block copolymer is bound to adriamycin via an amide bond, the efficacy is questionable since the release of the drug by hydrolysis is slow due to the amide bond, a chemically stable binding form.

Taxane compounds such as paclitaxel and docetaxel are useful anti-cancer agents, and thus there is a demand for novel derivatives which are water-soluble and have excellent anti-cancer activity.

Means for Solving the Problems

As a result of intensive studies for solving the problems described above, the present inventors have found a phenomenon that, when a compound having an alcoholic hydroxyl group is ester-bonded to a free carboxylic acid of succinic acid monoamide, the compound having the alcoholic hydroxyl group is easily released as the structure of succinic acid monoamide changes to a cyclized structure (succinic acid imide). On the basis of this, the present inventors produced a taxane-polymer conjugate in which a polymer having a polyethylene glycol moiety and a succinic acid monoamide moiety is ester-bonded to a taxane and found that the polymer conjugate thus obtained releases the taxane without depending on hydrolyzing enzymes, thereby completing the present invention.

Specifically, the present invention relates to the following (1) to (10).

(1) A taxane-polymer conjugate in which a carboxylic acid group of a polymer having a polyethylene glycol moiety and two or more succinic acid monoamide moieties is ester-bonded to an alcoholic hydroxyl group of a taxane.

(2) The taxane-polymer conjugate according to (1) above, wherein the polymer having a polyethylene glycol moiety and two or more succinic acid monoamide moieties is a block copolymer.

(3) The taxane-polymer conjugate according to (2) above, wherein the two or more succinic acid monoamide moieties form polyaspartic acid.

(4) The taxane-polymer conjugate according to (3) above, represented by the general formula (I)

[Chemical Formula 1]

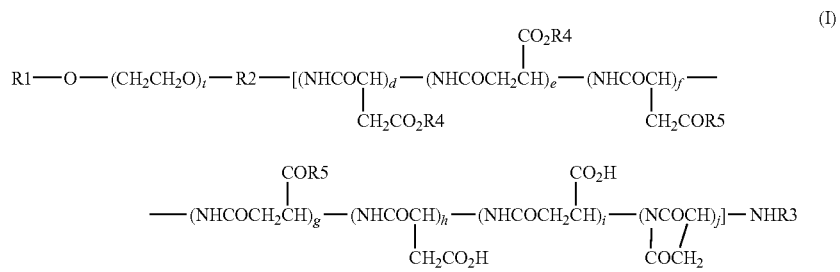

wherein R1 represents a hydrogen atom or a (C1-C6) alkyl group; R2 represents a linking group; R3 represents a hydrogen atom or a (C1-C6) acyl group; R4 represents a residue of an alcoholic hydroxyl group of a taxane; R5 represents a group selected from the group consisting of a (C1-C30) alkoxy group, a (C1-C30) aralkyloxy group, a (C1-C30) alkylamino group, a di(C1-C30) alkylamino group, an amino acid with a protected carboxyl group and —N(R6)CONH(R7) wherein R6 and R7, which may be identical or different, each represent a (C3-C6) cycloalkyl group, or a (C1-C5) alkyl group optionally substituted with a tertiary amino group; t represents an integer from 5 to 11,500; d, e, f, g, h, i and j each independently represent an integer from 0 to 200; provided that d+e is an integer from 1 to 200, and d+e+f+g+h+i+j is an integer from 3 to 200; and the respective constituent units of the polyaspartic acid are bound in any order.

(5) The taxane-polymer conjugate according to (4) above, wherein R1 is a (C1-C6) alkyl group; R2 is a (C2-C6) alkylene group; R3 is a (C1-C6) acyl group; t is an integer from 100 to 300; and d, e, f, g, h, i and j are each independently an integer from 0 to 100; provided that d+e is an integer from 1 to 100, and d+e+f+g+h+i+j is an integer from 6 to 100.

(6) The taxane-polymer conjugate according to (5) above, wherein R1 is a (C1-C3) alkyl group; R2 is a (C2-C4) alkylene group; R3 is a (C1-C3) acyl group; t is an integer from 100 to 300; and d, e, f, g, h, i and j each independently represent an integer from 0 to 90; provided that d+e is an integer from 1 to 90, and d+e+f+g+h+i+j is an integer from 15 to 90.

(7) The taxane-polymer conjugate according to any one of (1) to (6) above, wherein the taxane is paclitaxel or docetaxel.

(8) A taxane-polymer conjugate, obtained by ester-bonding a carboxylic acid group of a polymer having a polyethylene glycol moiety and two or more succinic acid monoamide moieties to an alcoholic hydroxyl group of a taxane, using a dehydrating condensing agent in an organic solvent.

(9) A method for producing the taxane-polymer conjugate according to any one of (1) to (7) above, the method comprising ester-bonding a carboxylic acid group of a polymer having a polyethylene glycol moiety and two or more succinic acid monoamide moieties to an alcoholic hydroxyl group of a taxane, using a dehydrating condensing agent in an organic solvent.

(10) An anti-cancer agent comprising the taxane-polymer conjugate according to any one of (1) to (8) above, as an active ingredient.

Effect of the Invention

The polymer conjugate of a taxane of the present invention is capable of releasing the taxane without depending on hydrolyzing enzymes in the body, is hardly affected by individual difference, and can be expected to have efficacious therapeutic effects.

BEST MODE FOR CARRYING OUT THE INVENTION

The polymeric derivative of a taxane of the present invention is characterized in that a carboxylic acid group of a polymer having a polyethylene glycol moiety and two or more succinic acid monoamide moieties is ester-bonded to an alcoholic hydroxyl group of a taxane.

According to the present invention, the term "succinic acid monoamide moiety" means the structure —NHCO—C—C—CO$_2$H, and the examples include succinic acid monoamide (—HNCO—CH$_2$—CH$_2$—CO$_2$H), a structure in which one of the two carboxylic acid groups in aspartic acid is amidated (—HNCO—CH(—NH—)—CH$_2$—CO$_2$H or —HNCO—CH$_2$—CH(—NH—)—CO$_2$H), or the like. These succinic acid monoamide moieties may constitute a polymer backbone, for example, as in the case of polyaspartic acid, or may also be bound to functional groups of the backbone polymer composed of a polyalcohol such as dextran, a polyamine such as polylysine, or a polycarboxylic acid other than polyaspartic acid (for example, polylactic acid and the like).

Examples of the polymer having a polyethylene glycol moiety and two or more succinic acid monoamide moieties include a graft-type polymer in which the polyethylene glycol moiety or succinic acid monoamide moiety branch from the polymer backbone in a comb-like form, and a block-type polymer (block copolymer) in which the polymer having a polyethylene glycol moiety and the succinic acid monoamide moiety are bound tandemly.

When two or more succinic acid monoamide moieties form polyaspartic acid, graft-type polymers also include a polymer in which polyethylene glycol moieties are partially bound to the polyaspartic acid backbone, and the like, while block-type polymers include a polymer in which the terminal of the polyaspartic acid is bound to the terminal of the polyethylene glycol moiety, and the like.

The polyethylene glycol moiety in a polymer of the taxane-polymer conjugate of the present invention includes polyethylene glycols having one or both terminals modified. When both of the terminals are modified, the modifying groups may be identical or different. Examples of the modifying group include a (C1-C6) alkyl group optionally having a substituent. Examples of the alkyl group in the (C1-C6) alkyl group optionally having a substituent include alkyl groups enumerated below, and preferred is a (C1-C4) alkyl group, including, for example, a methyl group, an ethyl group, an n-propyl group, an n-butyl group, and the like. Examples of the substituent in the (C1-C6) alkyl group optionally having a substituent include, for example, an amino group, a methylamino group, a dimethylamino group, an ethylamino group, a diethylamino group, and the like.

The molecular weight of the polyethylene glycol moiety is about 300 to 500,000, preferably about 500 to 100,000, more preferably about 1,000 to 50,000.

The molecular weight of the polymer having a polyethylene glycol moiety and two or more succinic acid monoamide moieties according to the present invention is about 500 to 500,000, preferably about 600 to 100,000, more preferably about 800 to 80,000.

According to the present invention, the term "molecular weight" refers to a weight average molecular weight determined by the GPC method.

In the taxane-polymer conjugate of the present invention, the amount of the taxane bound to the polymer having a polyethylene glycol moiety and two or more succinic acid monoamide moieties is 1 to 100%, preferably 1 to 90%, more preferably 2 to 60%, based on the total number of carboxylic acid groups.

According to the present invention, taxanes are not particularly limited, provided that they are compounds with the taxane skeleton having an alcoholic hydroxyl group and an anti-cancer activity. Examples of the taxanes include paclitaxel represented by formula (II), docetaxel represented by formula (III) and the like. The alcoholic hydroxyl group in taxanes is, for example, the hydroxyl group at the 2'-position or the like in formula (II), but the substituent position is not limited provided that the hydroxyl group is an alcoholic hydroxyl group.

[Chemical Formula 2]

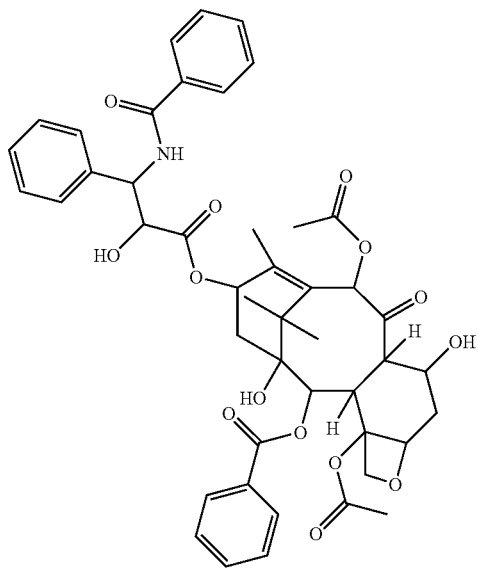

(II)

[Chemical Formula 3]

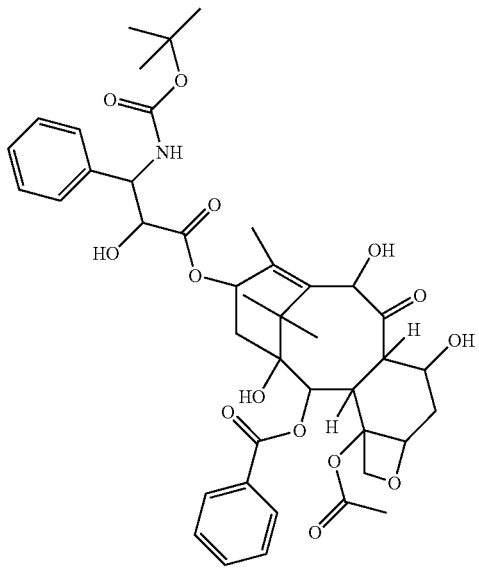

(III)

According to the present invention, the two or more succinic acid monoamide moieties are preferably polyaspartic acid.

The preferred taxane-polymer conjugate of the present invention includes a compound represented by the general formula (I), wherein R1 represents a hydrogen atom or a (C1-C6) alkyl group; R2 represents a linking group; R3 represents a hydrogen atom or a (C1-C6) acyl group; R4 represents an alcoholic hydroxyl group in taxanes; R5 represents a group selected from the group consisting of a (C1-C30) alkoxy group, a (C1-C30) aralkyloxy group, a (C1-C30) alkylamino group, a di(C1-C30) alkylamino group, an amino acid with a protected carboxyl group, and —N(R6) CONH(R7) wherein R6 and R7, which may be identical or different, each represent a (C3-C6) cycloalkyl group, or a (C1-C5) alkyl group optionally substituted with a tertiary amino group; t represents an integer from 5 to 11,500; d, e, f, g, h, i and j each independently represent an integer from 0 to 200; provided that d+e represents an integer from 1 to 200, and d+e+f+g+h+i+j represents an integer from 3 to 200; and the respective constituent units of the polyaspartic acid are bound in any order.

Examples of the (C1-C6) alkyl group for R1 in the general formula (I) include a straight-chain or branched (C1-C6) alkyl group, and preferred is a straight-chain or branched (C1-C4) alkyl group, and particularly preferred is a straight-chain or branched (C1-C3) alkyl group. Examples of the straight-chain or branched (C1-C6) alkyl group include a methyl group, an ethyl group, an n-propyl group, an i-propyl group, an n-butyl group, a t-butyl group and the like. Particularly preferred are a methyl group, an ethyl group, an n-propyl group and an i-propyl group, and preferred is a methyl group among them.

Examples of the linking group represented by R2 in the general formula (I) include, but are not particularly limited to, a (C2-C6) alkylene group. Preferred is a (C2-C4) alkylene group including, for example, an ethylene group, a trimethylene group, a butylene group and the like, and particularly preferred is a trimethylene group.

Examples of the (C1-C6) acyl group for R3 in the general formula (I) include, but are not particularly limited to, a formyl group, an acetyl group, a propionyl group, a pivaloyl group and the like, and preferred is an acetyl group.

With regard to the residue of the alcoholic hydroxyl group in taxanes for R4 in the general formula (I), examples of taxanes include the aforementioned taxanes and are not particularly limited provided that the taxanes have an alcoholic hydroxyl group capable of binding to a carboxylic acid moiety of a polymer via an ester bond by using a dehydrating condensing agent and have an anti-cancer activity. Examples of the taxanes include paclitaxel represented by formula (II), docetaxel represented by formula (III) and the like.

R5 in the general formula (I) represents a group selected from the group consisting of a (C1-C30) alkoxy group, a (C1-C30) aralkyloxy group, a (C1-C30) alkylamino group, a di(C1-C30) alkylamino group, an amino acid with a protected carboxyl group, and —N(R6)CONH(R7) wherein R6 and R7, which may be identical or different, area (C3-C6) cycloalkyl group, or a (C1-C5) alkyl group optionally substituted with a tertiary amino group. R5 in the general formula (I) may be identical or different in one molecule, and a polymer in the polymer conjugate of taxanes may include a single type or a mixed type of R5.

Examples of the (C1-C30) alkoxy group include a straight-chain or branched (C1-C30) alkoxy group, and preferred is a straight-chain or branched (C1-C10) alkoxy group, including, for example, a methoxy group, an ethoxy group, an n-propoxy group, an i-propoxy group, an n-butoxy group, a t-butoxy group and the like. Examples of the (C1-C30) aralkyloxy group include a straight-chain or branched (C1-C30) aralkyloxy group, and preferred is a straight-chain or branched (C1-C10) aralkyloxy group, including, for example, a 4-phenylbutoxy group and the like.

Examples of the (C1-C30) alkylamino group or di(C1-C30) alkylamino group include a straight-chain or branched (C1-C30) alkylamino group or a di(C1-C30) alkylamino group, and preferred is a straight-chain or branched (C1-C20) alkylamino group or a di(C1-C20) alkylamino group, including, for example, a methylamino group, an ethylamino group, an n-propylamino group, an i-propylamino group, an n-butylamino group, a t-butylamino group, a dimethylamino group, a diethylamino group, a dibutylamino group and the like.

Examples of the amino acid with a protected carboxyl group include an amino acid usually used in peptide synthesis, in which a carboxyl group is protected, including, for example, a phenylalanine benzyl ester and the like.

Examples of the group —N(R6) CONH(R7) [wherein R6 and R7, which may be identical or different, are a (C3-C6) cycloalkyl group or a (C1-C5) alkyl group optionally substituted with a tertiary amino group] include, but are not particularly limited to, for example, a cyclohexylaminocarbonylcyclohexylamino group, an isopropylaminocarbonylisopropylamino group, and the like.

Polyaspartic acid which is composed of two or more succinic acid monoamide moieties in the taxane-polymer conjugate represented by the general formula (I) of the present invention, includes constituent units of α-amino acid type, β-amino acid type, cyclized type and the like. These constituent units are bound in any order, and may be bound to form a block-type form or a random-type form.

The total number of aspartic acid residues in the polyaspartic acid of the polymer conjugate of taxanes represented by the general formula (I), which is represented by "d+e+f+g+h+i+j", is about 3 to 200, preferably about 6 to 100, particularly preferably 15 to 90.

The proportion of the number of aspartic acid residues bound to taxane (d+e) based on the total number of aspartic acid residues (d+e+f+g+h+i+j) is 1 to 100%, preferably 3 to 90%, more preferably 4 to 60%. Furthermore, the number of aspartic acid residues (d+e) is about 1 to 200, preferably about 1 to 100, particularly preferably about 1 to 90.

The proportion of the α-amino acid type aspartic acid residues (d+f+h) based on the total number of aspartic acid residues (d+e+f+g+h+i+j) is 10 to 100%, preferably 20 to 100%. The proportion can be appropriately changed, for example, by selecting the deprotection conditions for the protecting group in the polyaspartic acid and the like.

t in the general formula (I) is an integer of about 5 to 11,500, preferably an integer of about 8 to 2,300, more preferably an integer of about 100 to 300.

The taxane-polymer conjugate represented by the general formula (I) may form micelles with the polyethylene glycol moiety as an outer shell in water.

The taxane-polymer conjugate of the present invention is obtained, for example, by ester-bonding a carboxylic acid group of a polymer having a polyethylene glycol moiety and two or more succinic acid monoamide moieties to an alcoholic hydroxyl group of a taxane using a dehydrating condensing agent in an organic solvent, and the present invention also includes the production method; that is, a method of subjecting, for example, a block copolymer of polyethylene glycol moiety-polyaspartic acid prepared according to the method described in Patent Document 4 and a taxane in which functional groups other than the groups to be reacted are protected if necessary, to a reaction using a dehydrating condensing agent such as dicyclohexylcarbodiimide (DCC), diisopropylcarbodiimide (DIPC), 1-ethyl-3-(3-dimethylaminopropyl)carbodiimide hydrochloride (WSC) or 1-ethoxycarbonyl-2-ethoxy-1,2-dihydroxyquinolinone (EEDQ) in an organic solvent with the two substances dissolved therein, preferably in an aprotic polar solvent such as N, N-dimethylformamide (DMF), 1,3-dimethyl-2-imidazolidinone (DMI) or N-methylpyrrolidone (NMP), at 0 to 180° C., preferably at 5 to 50° C. Furthermore, a reaction aid such as N,N-dimethylaminopyridine (DMAP) may be used in the condensation reaction. After the condensation reaction, deprotection is carried out as necessary, and conventional procedures for separation and purification and the like can be applied to obtain a taxane-polymer conjugate.

In addition, a taxane-polymer conjugate in which R5 is the group —N(R6)CONH(R7) (wherein R6 and R7, which may be identical or different, are each a (C3-C6) cycloalkyl group, or a (C1-C5) alkyl group optionally substituted with a tertiary amino group) can be obtained also by a reaction using the aforementioned carbodiimides as a condensing agent.

As a method of introducing as R5 a (C1-C30) alkoxy group, a (C1-C30) aralkyloxy group, a (C1-C30) alkylamino group, a di(C1-C30) alkylamino group or an amino acid with a protected carboxyl group into a compound of general formula (I), there can be mentioned a method in which a carboxylic acid group of a polymer is first activated by the method as described above and then reacted with a corresponding alcohol, a corresponding amine or an amino acid with a protected carboxyl group and the like in an amount to be introduced under a basic condition; a method in which a corresponding alcohol, a corresponding amine, an amino acid with a protected carboxyl group and the like are first activated and then reacted with a polymer; and the like. After the purification of the polymer, it is possible to re-activate an unreacted carboxylic acid group in the polymer by the same reaction, and an alcoholic hydroxyl group in taxanes may be condensed to the re-activated carboxylic acid group. Alternatively, other alcohols, amines and the like may be repeatedly reacted to synthesize a mixture of polymers having various substituents R5, to which an alcoholic hydroxyl group of taxanes may subsequently be condensed. Furthermore, after condensation of taxanes, a (C1-C30) alkoxy group, a (C1-C30) aralkyloxy group, a (C1-C30) alkylamino group, a di(C1-C30) alkylamino group, an amino acid with a protected carboxyl group or the like may be introduced.

The method for producing the taxane-polymer conjugate of the present invention is not intended to be limited to the aforementioned methods.

The taxane-polymer conjugate of the present invention can be used as an anti-cancer agent. The polymer conjugate can be used in a dosage form which is conventionally used, including, for example, injection, tablet, powder and the like. In formulation, pharmaceutically acceptable carriers conventionally used, for example, binding agents, lubricants, disintegration agents, solvents, excipients, solubilizing agents, dispersing agents, stabilizing agents, suspending agents, preservatives, soothing agents, colorants, flavors, and the like can be used. The use as an injection is preferred, and usually, for example, water, physiological saline, a 5% glucose or mannitol solution, water-soluble organic solvents (for example, glycerol, ethanol, dimethylsulfoxide, N-methylpyrrolidone, polyethylene glycol, cremophor and the like, and mixtures thereof), mixtures of water and the water-soluble organic solvents, and the like are used.

The dosage of the taxane-polymer conjugate of the present invention can vary as a matter of course, depending on the sex, age, physiological conditions, pathogenic conditions and the like of patients, and the polymer conjugate is parenterally administered, typically at a dose of 0.01 to 500 mg/m$^2$, preferably 0.1 to 250 mg/m$^2$ as an active ingredient per day for an adult. Administration by injection is conducted intravenously, intra-arterially, in the affected site (tumor site) and the like.

EXAMPLES

Hereinafter, the present invention will be illustrated more specifically with reference to Examples, but is not intended to be limited to these Examples.

Example 1

Synthesis of compound 1 (conjugate of paclitaxel and a block copolymer comprising a methoxypolyethylene glycol moiety having a molecular weight of 12,000 and a polyaspartic acid moiety having a polymerization number of 35: general formula (I) in which R1=Me (methyl group), R2=trimethylene group, R3=Ac (acetyl group), R4=paclitaxel residue, R5=isopropylaminocarbonylisopropylamino group, d+e+f+g+h+i+j=35, t=273)

A methoxypolyethylene glycol-polyaspartic acid block copolymer (polymerization number of aspartic acid: 35, 15.4 mg) prepared according to the method described in Patent Document 4 and commercially available paclitaxel (10 mg) were dissolved in DMF (1 ml), and DMAP (0.8 mg) and DIPC (0.01 ml) were added thereto. The mixture was stirred for 20 hours at 25° C. Ethanol (3 ml) and diisopropyl ether (12 ml) were added to the reaction liquid, and the mixture was stirred for 30 minutes at room temperature. Subsequently, the precipitate was collected by filtration, and washed with ethanol/diisopropyl ether (1/4 (v/v), 3 ml). The resultant precipitate was dissolved in acetonitrile/water (1/1 (v/v), 3 ml), and then the solution was passed through a column of an ion-exchange resin (Dowex 50 (H$^+$) manufactured by Dow Chemical Company, 0.2 ml), and eluted with acetonitrile/water (1/1 (v/v), 1 ml). After water (2 ml) was added to the eluted fraction thus obtained, acetonitrile was distilled off under reduced pressure, and then the residue was freeze-dried to obtain compound 1 (18.2 mg).

On the basis of the amount of unreacted paclitaxel in the reaction liquid determined by HPLC (high performance liquid chromatography), the content of paclitaxel in compound 1 was determined as 19.5% (w/w), and the ratio of (d+e) based on (d+e+f+g+h+i+j) was determined as 13%. In compound 1, free paclitaxel was not detected.

According to this method, an isopropylaminocarbonylisopropylamino group can be added as R5, and the abundance ratio of the group is determined by $^1$H-NMR (hydrogen nuclear magnetic resonance spectrum) using compound 1 dissolved in sodium deuteroxide/deuterium oxide/deuterated acetonitrile. The ratio of the isopropylaminocarbonylisopropylamino group to the polyaspartic acid, that is, the ratio of (f+g) based on (d+e+f+g+h+i+j) was 3.1%. The remaining aspartic acid residues are in the form of a free carboxylic acid (h+i) or a cyclic structure (j).

Example 2

Synthesis of compound 2 (conjugate of docetaxel and a block copolymer comprising a methoxypolyethylene glycol moiety having a molecular weight of 12,000 and a polyaspartic acid moiety having a polymerization number of 33: general formula (I) in which R1=Me (methyl group), R2=trimethylene group, R3=Ac (acetyl group), R4=docetaxel residue, R5=isopropylaminocarbonylisopropylamino group, d+e+f+g+h+i+j=33, t=273)

A methoxypolyethylene glycol-polyaspartic acid block copolymer (polymerization number of aspartic acid: 33, 665.4 mg) prepared according to the method described in Patent Document 4 and commercially available docetaxel (300 mg) were dissolved in DMF (10 ml), and DMAP (18.5 mg) and DIPC (0.47 ml) were added thereto. The mixture was stirred for 20 hours at 15° C., and then further stirred for 4 hours at 25° C. Ethyl acetate (15 ml), ethanol (15 ml) and diisopropyl ether (120 ml) were added to the reaction liquid, and the mixture was stirred for 30 minutes at room temperature. Subsequently, the precipitate was collected by filtration, and washed with ethanol/diisopropyl ether (1/4 (v/v), 20 ml). The resultant precipitate was dissolved in acetonitrile/water (1/1 (v/v), 60 ml), and then the solution was passed through a column of an ion-exchange resin (Dowex 50 (H$^+$) manufactured by Dow Chemical Company, 5 ml), and eluted with acetonitrile/water (1/1 (v/v), 10 ml). After water (50 ml) was added to the eluted fraction thus obtained, acetonitrile was distilled off under reduced pressure, and then the residue was freeze-dried to obtain compound 2 (850 mg).

On the basis of the amount of unreacted docetaxel in the reaction liquid determined by HPLC (high performance liquid chromatography), the content of docetaxel in compound 2 was determined as 26.5% (w/w), and the ratio of (d+e) based on (d+e+f+g+h+i+j) was determined as 21%. In compound 2, free docetaxel was not detected.

According to this method, an isopropylaminocarbonylisopropylamino group can be added as R5, and the abundance ratio of the group is determined by $^1$H-NMR (hydrogen nuclear magnetic resonance spectrum) using compound 2 dissolved in sodium deuteroxide/deuterium oxide/deuterated acetonitrile. The ratio of the isopropylaminocarbonylisopropylamino group to the polyaspartic acid, that is, the ratio of (f+g) based on (d+e+f+g+h+i+j), was 20%. The remaining aspartic acid residues are in the form of free carboxylic acid (h+i) or a cyclic structure (j).

Example 3

Synthesis of compound 3 (conjugate of docetaxel and a block copolymer comprising a methoxypolyethylene glycol moiety having a molecular weight of 12,000 and a polyaspartic acid moiety having a polymerization number of 21 and a binding mode of α-binding type: general formula (I) in which R1=Me (methyl group), R2=trimethylene group, R3=Ac (acetyl group), R4=docetaxel residue, R5=isopropylaminocarbonylisopropylamino group, d+f+h+j=21, e=0, g=0, i=0, t=273)

A methoxypolyethylene glycol-polyaspartic acid block copolymer (polymerization number of aspartic acid: 21, binding mode of aspartic acid is α-binding, 259.7 mg) prepared according to Reference Example 1 describedbelow and commercially available docetaxel (100 mg) were dissolved in DMF (3 ml), and DMAP (5.1 mg) and DIPC (0.13 ml) were added thereto. The mixture was stirred for 44 hours at 15° C., and then further stirred for 5 hours at 25° C. Ethyl acetate (4 ml), ethanol (4 ml) and diisopropyl ether (40 ml) were added to the reaction liquid, and the mixture was stirred for 30 minutes at room temperature. Subsequently, the precipitate was collected by filtration, and washed with ethanol/diisopropyl ether (1/4 (v/v), 5 ml). The resultant precipitate was dissolved in acetonitrile/water (1/1 (v/v), 20 ml), and then the solution was passed through a column of an ion-exchange resin (Dowex 50(H$^+$) manufactured by Dow Chemical Company, 3 ml), and eluted with acetonitrile/water (1/1 (v/v), 6 ml). After water (10 ml) was added to the eluted fraction thus obtained, acetonitrile was distilled off under reduced pressure, and then the residue was freeze-dried to obtain compound 3 (320 mg).

On the basis of the amount of unreacted docetaxel in the reaction liquid measured by HPLC (high performance liquid chromatography), the content of docetaxel in compound 3 was determined as 22.8% (w/w), and the ratio of (d) based on (d+f+h+j) was determined as 25%. In compound 3, free docetaxel was not detected.

According to this method, an isopropylaminocarbonylisopropylamino group can be added as R5, and the abundance ratio of the group is determined by $^1$H-NMR (hydrogen nuclear magnetic resonance spectrum) using compound 3 dissolved in sodium deuteroxide/deuterium oxide/deuterated acetonitrile. The ratio of the isopropylaminocarbonylisopropylamino group to the polyaspartic acid, that is, the ratio of (f) based on (d+f+h+j) was 37%. The remaining aspartic acid residues are in the form of a free carboxylic acid (h) or a cyclic structure (j).

Example 4

Synthesis of compound 4 (conjugate of docetaxel and a block copolymer comprising a methoxypolyethylene glycol moiety having a molecular weight of 12,000 and a polyaspartic acid moiety having a polymerization number of 33: general formula (I) in which R1=Me (methyl group), R2=trimethylene group, R3=Ac (acetyl group), R4=docetaxel residue, R5=isopropylaminocarbonylisopropylamino group and O-benzyl-phenylalanyl group, d+e+f+g+h+i+j=33, t=273)

A methoxypolyethylene glycol-polyaspartic acid block copolymer (polymerization number of aspartic acid: 33, 326.2 mg) prepared according to the method described in Patent Document 4 and commercially available docetaxel (100 mg) were dissolved in DMF (7 ml), and DMAP (9 mg) and DIPC (0.07 ml) were added thereto. The mixture was stirred for 20 hours at 15° C. Phenylalanine benzyl ester hydrochloride (23.7 mg), triethylamine (0.01 ml) and DIPC (0.17 ml) were added, and the mixture was stirred further for 20 hours at 15° C., and then further stirred for 4 hours at 25° C. Ethyl acetate (11 ml), ethanol (11 ml) and diisopropyl ether (88 ml) were added to the reaction liquid, and the mixture was stirred for 30 minutes at room temperature. Subsequently, the precipitate was collected by filtration, and washed with ethanol/diisopropyl ether (1/4 (v/v), 20 ml). The resultant precipitate was dissolved in acetonitrile/water (1/1 (v/v), 20 ml), and then the solution was passed through a column of an ion-exchange resin (Dowex 50 (H+) manufactured by Dow Chemical Company, 3 ml), and eluted with acetonitrile/water (1/1 (v/v), 20 ml). After water (25 ml) was added to the eluted fraction thus obtained, acetonitrile was distilled off under reduced pressure, and then the residue was freeze-dried to obtain compound 4 (390 mg).

On the basis of the amount of unreacted docetaxel in the reaction liquid determined by HPLC (high performance liquid chromatography), the content of docetaxel in compound 4 was determined as 19.3% (w/w), and the ratio of (d+e) based on (d+e+f+g+h+i+j) was determined as 15%. In compound 4, free docetaxel was not detected.

The O-benzyl-phenylalanyl group introduced as one of R5 is determined by quantifying the amount of benzyl alcohol released by hydrolyzing compound 4 in acetonitrile-aqueous sodium hydroxide solution at 40° C. for 6 hours. The ratio of the O-benzyl-phenylalanyl group to the polyaspartic acid, that is, the ratio of the O-benzyl-phenylalanyl group bound to (f+g) based on (d+e+f+g−h+i+j) was 8%.

According to this method, an isopropylaminocarbonylisopropylamino group can be added as R5, and the abundance ratio of the group is determined by $^1$H-NMR (hydrogen nuclear magnetic resonance spectrum) using a solution of the compound 4 in sodium deuteroxide/deuterium water/deuterated acetonitrile. The ratio of the isopropylaminocarbonylisopropylamino group in the polyaspartic acid, that is, the ratio of the group bound to (f+g) based on (d+e+f+g+h+i+j) was 12%. As a result, the ratio of the total amount of R5 to the polyaspartic acid, that is, the ratio of (f+g) based on (d+e+f+g+h+i+j) was 20%. The remaining aspartic acid residues are in the form of a free carboxylic acid (h+i) or a cyclic structure (j).

Comparative Example

Synthesis of a comparative compound (conjugate of paclitaxel and a block copolymer comprising a methoxypolyethylene glycol moiety having a molecular weight of 12,000 and a polyglutamic acid moiety having a polymerization number of 22)

A methoxypolyethylene glycol-polyglutamic acid block copolymer (22 mg) prepared according to the method described in Japanese Patent Application Laying Open (KOKAI) No. 5-955 and commercially available paclitaxel (10 mg) were dissolved in DMF (1 ml), and DMAP (0.83 mg) and DIPC (0.01 ml) were added thereto. The mixture was stirred for 20 hours at 25° C. Ethanol (1.5 ml) and diisopropyl ether (12 ml) were added to the reaction liquid, and the mixture was stirred for 30 minutes at room temperature. Subsequently, the precipitate was collected by filtration, and washed with ethanol/diisopropyl ether (1/4 (v/v), 2 ml). The resultant precipitate was dissolved in acetonitrile/water (1/1 (v/v), 3 ml), and then the solution was passed through a column of an ion-exchange resin (Dowex 50 (H+) manufactured by Dow Chemical Company, 0.2 ml), and eluted with acetonitrile/water (1/1 (v/v), 1 ml). After water (1 ml) was added to the eluted fraction thus obtained, acetonitrile was distilled off under reduced pressure, and then the residue was freeze-dried to obtain the comparative compound (29.0 mg).

On the basis of the amount of unreacted paclitaxel in the reaction liquid determined by HPLC, the content of paclitaxel in the comparative compound was determined as 30.2% (w/w). In the comparative compound, free paclitaxel was not detected.

Test Example 1

Drug Release from Paclitaxel Conjugates in the Absence of Enzymes

Compound 1 or the comparative compound was dissolved in PBS (phosphate buffered physiological saline; pH 7.1) to a polymer concentration of 1 mg/ml, and the solution was incubated at 37° C. Paclitaxel hydrolyzed and released from the polymer conjugate was separated and quantified by HPLC in comparison with a standard curve. The percentage of the quantified value based on the total drug amount determined from the drug content of the polymer conjugate is shown in FIG. 1.

As is obvious from FIG. 1, the polymer conjugate of the present invention (compound 1) released 75% or more of paclitaxel for 24 hours in the absence of hydrolyzing enzymes, whereas the comparative compound not having a succinic acid monoamide moiety did not release paclitaxel even after 24 hours. This result demonstrates the excellent drug release performance of the polymer conjugate of the present invention in the absence of enzymes.

Test Example 2

Drug Release from Docetaxel Conjugates in the Absence of Enzymes

Compounds 2 and 3 and compound 4 were each dissolved in PBS (phosphate buffered physiological saline; pH 7.1) to a polymer concentration of 1 mg/ml, and the solution was incubated at 37° C. Docetaxel hydrolyzed and released from the polymer conjugate was separated and quantified by HPLC in comparison with a standard curve. The percentage of the quantified value based on the total drug amount determined from the drug content of the polymer conjugate is shown in FIG. 2.

As is obvious from FIG. 2, the polymer conjugates of the present invention (compounds 2, 3 and 4) released 20% or more of paclitaxel for 24 hours in the absence of hydrolyzing enzymes. This result demonstrates the excellent drug release performance of the polymer conjugates of the present invention in the absence of enzymes.

Test Example 3

Antitumor Effect of Compound 1

Mouse colon cancer, Colon26, maintained by serial subcutaneous subculture in mice was minced into about 2-mm square fragments, and the fragments were subcutaneously transplanted on the dorsal part of female CDF1 mice with a trocar. Seven days after tumor transplantation, the polymer conjugate of the present invention (compound 1) or the control drug (paclitaxel, PTX) was administered intravenously to the mouse tail vein three times at an interval of 4 days (Day 0, Day 4 and Day 8 in Table 1) at a dose of 200 mg/kg as PTX. The compound 1 was dissolved in a 5% glucose solution for injection and used. PTX was dissolved in anhydrous ethanol and cremophor (manufactured by Sigma Co., Ltd) and diluted with physiological saline at the time of use. After the administration, the major axis (L mm) and minor axis (W mm) of the tumor were measured using a caliper, and the volume of the tumor was calculated by the formula: $(L \times W^2)/2$. Table 1 shows the relative tumor volume based on the tumor volume on the day of administration initiation.

TABLE 1

| | | Days after administration initiation | | | |
|---|---|---|---|---|---|
| | | 0 | 4 | 8 | 11 |
| Compound 1 | Relative tumor volume | 1 | 1.9 | 2.25 | 2.24 |
| Paclitaxel | Relative tumor volume | 1 | 3.28 | 4.75 | 4.07 |
| Control | Relative tumor volume | 1 | 4.47 | 8.1 | 14.62 |

Table 1 demonstrates that the polymer conjugate of the present invention has a superior anti-cancer activity over PTX at a dose equivalent to that of PTX, and therefore can serve as an anti-cancer agent.

Test Example 4

Antitumor Effect of Compounds 2 and 3

Mouse colon cancer, Colon26, maintained by serial subcutaneous subculture in mice was minced into about 2-mm square fragments, and the fragments were subcutaneously transplanted on the dorsal part of female CDF1 mice with a trocar. Seven days after tumor transplantation, the polymer conjugates of the present invention (compound 2 and compound 3) and the control drug (docetaxel, DTX) were each intravenously administered once to the mouse tail vein at the respective maximum tolerance dose. The compound 2 and compound 3 were dissolved in 5% glucose solution for injection to a level for the use at a dose of 200 mg/kg as DTX. DTX to be used was prepared by dissolving a commercially available Taxotere injection (for 100 mg/kg use) in a vehicle solution attached to the product, and diluting it with physiological saline at the time of use. After the administration, the major axis (L mm) and minor axis (W mm) of the tumor were measured using a caliper, and the tumor volume was calculated by the formula: $(L \times W^2)/2$. Table 2 shows the relative tumor volume based on the tumor volume on the day of administration initiation.

TABLE 2

| | | Days after administration | | | |
|---|---|---|---|---|---|
| | Dose | 0 | 2 | 4 | 7 | 10 |
| Compound 2 | 200 mg/kg | 1.00 | 1.31 | 1.26 | 1.23 | 0.92 |
| Compound 3 | 200 mg/kg | 1.00 | 1.33 | 1.56 | 1.59 | 1.23 |
| DTX | 100 mg/kg | 1.00 | 1.61 | 1.57 | 2.30 | 5.85 |
| Control | | 1.00 | 2.89 | 6.09 | 9.38 | 14.03 |

Table 2 demonstrates that the polymer conjugates of the present invention have a superior anti-cancer activity over DTX at the maximum tolerance dose, and can therefore serve as anti-cancer agents.

Test Example 5

Antitumor Effect of Compound 4

Mouse colon cancer, Colon26, maintained by serial subcutaneous subculture in mice was minced into about 2-mm square fragments, and these fragments were subcutaneously transplanted on the dorsal part of female CDF1 mice with a trocar. Seven days after tumor transplantation, the polymer conjugate of the present invention (compound 4) or the control drug (docetaxel, DTX) was intravenously administered once to the mouse tail vein at the maximum tolerance dose. The compound 4 was dissolved in a 5% glucose solution for injection at a level for the use at a dose of 200 mg/kg as DTX. DTX to be used was prepared by dissolving a commercially available Taxotere injection (for the use at a dose of 100 mg/kg use) with a vehicle solution attached to the product and diluting it with physiological saline at the time of use. After the administration, the major axis (L mm) and minor axis (W mm) of the tumor were measured using a caliper, and the tumor volume was calculated by the formula: $(L \times W^2)/2$. Table 3 shows the relative tumor volume based on the tumor volume on the day of administration initiation.

TABLE 3

|  | Dose | Days after administration | | | | |
|---|---|---|---|---|---|---|
|  |  | 0 | 3 | 5 | 7 | 10 |
| Compound 4 | 200 mg/kg | 1.00 | 1.09 | 0.99 | 0.88 | 0.53 |
| DTX | 100 mg/kg | 1.00 | 1.17 | 1.17 | 2.17 | 5.75 |
| Control |  | 1.00 | 3.37 | 6.03 | 9.17 | 15.79 |

Table 3 demonstrates that the polymer conjugate of the present invention has a superior anti-cancer activity over DTX at the maximum tolerance dose, and therefore can serve as an anti-cancer agent.

Reference Example 1

Synthesis of a Block Copolymer of Mono-Methoxypolyethylene Glycol Having a Molecular Weight of 12,000 and Polyaspartic Acid Having a Polymerization Number of 21 and Only α-Type Bindings A methoxypolyethylene glycol having an aminopropyl group at the end (SUNBRIGHT MEPA-12T, manufactured by Nippon Oil & Fats Co., Ltd., average molecular weight 12,000, 1.0 g) was dissolved in DMSO (20 ml), and β-benzyl L-aspartate N-carboxylic anhydride (0.47 g) was then added thereto. The mixture was stirred for 20 hours at 35° C. Ethanol (40 ml) and diisopropyl ether (160 ml) were added to the reaction liquid, and the mixture was stirred for 90 minutes at room temperature. Subsequently, the precipitate was collected by filtration, and washed with ethanol/diisopropyl ether (1/4 (v/v), 50 ml).

The resultant precipitate was dissolved in DMF (20 ml), and acetic anhydride (0.3 ml) was added. The mixture was stirred for 15 hours at room temperature. Ethanol (40 ml) and diisopropyl ether (160 ml) were added to the reaction liquid, and the mixture was stirred for 90 minutes at room temperature. Subsequently, the precipitate was collected by filtration, and washed with ethanol/diisopropyl ether (1/4 (v/v), 50 ml), to obtain 1.34 g of solid.

From the resultant solids, 1.24 g was dissolved in DMF (25 ml), then 5% palladium-carbon (120 mg) was added, and hydrogenolysis of the benzyl group was carried out overnight at room temperature. After 5% palladium-carbon in the reaction liquid was filtrated off, ethyl acetate (50 ml) and diisopropyl ether (280 ml) were added. The mixture was stirred for 90 minutes at room temperature. The precipitate was collected by filtration, washed with ethanol/diisopropyl ether (1/4 (v/v), 100 ml) and dried, and then the residue was dissolved in water (100 ml). The pH of the solution was adjusted to 10.0 using a 1 N aqueous sodium hydroxide solution, and then the resultant solution was passed through an HP-20 SS column (100 ml) sufficiently washed to perform column chromatography. The column was washed with water (300 ml) and then eluted with 50% hydrous acetonitrile (300 ml). The eluted fraction containing the desired compound was further passed through a column of an ion-exchange resin, Dowex 50W ($H^+$) (25 ml), and washed with 50% hydrous acetonitrile (75 ml). The eluted solution was concentrated under reduced pressure and then freeze-dried to obtain the desired compound (1.02 g).

$^1$H-NMR ($D_2O$+NaOD, ppm): 2.1 (s), 2.60 (dd), 2.71 (dd), 3.39 (s), 4.63 (dd)

The polymerization number of aspartic acid in this compound was 21, when quantified based on the titration value obtained by using 0.02 N sodium hydroxide.

Figure 1:
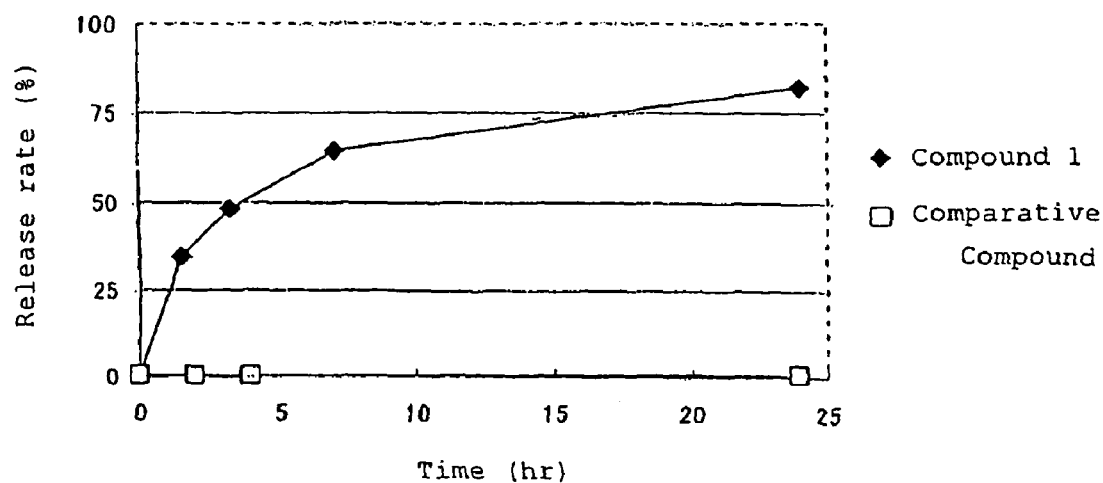
FIG. 1 shows the percentage of the amount of paclitaxel released from compound 1 (polyaspartic acid-paclitaxel conjugate) or the comparative compound (polyglutamic acid-paclitaxel conjugate) in a PBS solution (pH 7.1, 37° C.), based on the total amount of the bound drug.
Figure 2:
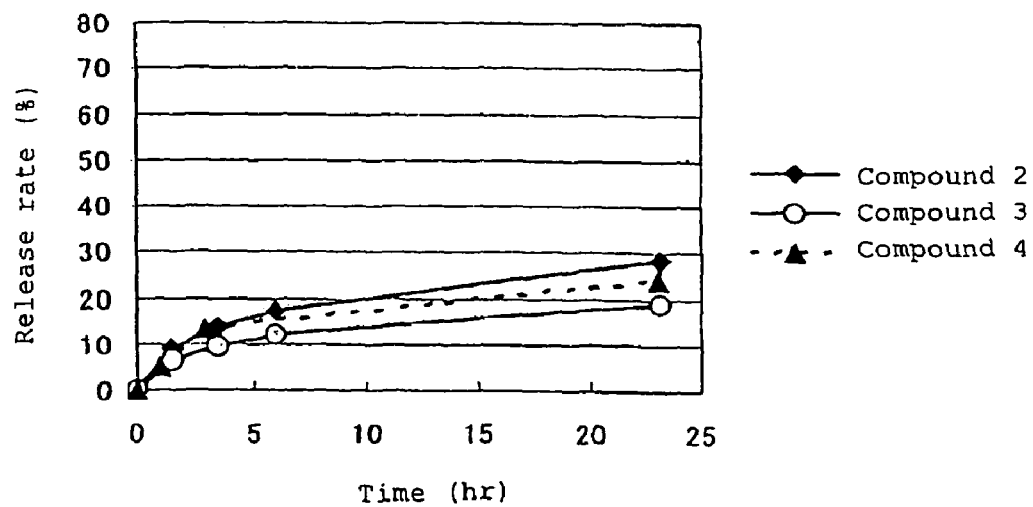
FIG. 2 shows the percentage of the amount of paclitaxel released from compound 2, 3 or compound 4 (polyaspartic acid-docetaxel conjugate) in a PBS solution (pH 7.1, 37° C.), based on the total amount of the bound drug.

The invention claimed is:
1. A paclitaxel or docetaxel polymer conjugate in which a carboxylic acid group of a block copolymer having a polyethylene glycol moiety and two or more amidated polyaspartic acid moieties is ester-bonded to an alcoholic hydroxyl group of a paclitaxel or docetaxel represented by formula (I)

[Chemical Formula 4]

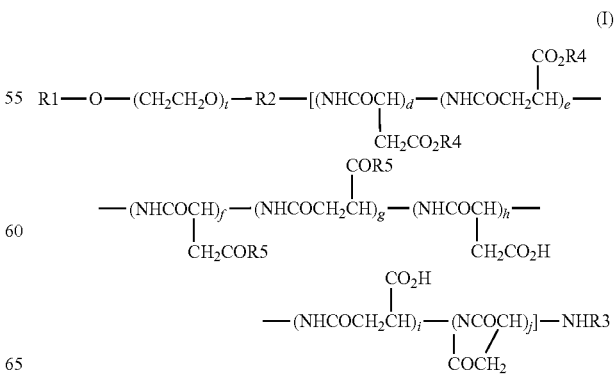

wherein R1 represents a hydrogen atom or a (C1-C6) alkyl group; R2 represents a linking group; R3 represents a hydrogen atom or a (C1-C6) acyl group; R4 represents a residue of an alcoholic hydroxyl group of a paclitaxel or docetaxel; R5 represents a group selected from the group consisting of a (C1-C30) alkoxy group, a (C1-C30) aralkyloxy group, a (C1-C30) alkylamino group, a di(C1-C30) alkylamino group, an amino acid with a protected carboxyl group and —N(R6)CONH(R7) wherein R6 and R7, which may be identical or different, each represent a (C3-C6) cycloalkyl group, or a (C1-C5) alkyl group which may be substituted with a tertiary amino group; t represents an integer from 5 to 11,500; d, e, f, g, h, i and j each independently represent an integer from 0 to 200; provided that d+e is an integer from 1 to 200, and d+e+f+g+h+i+j is an integer from 3 to 200; and the respective constituent units of the polyaspartic acid are bound in any order.

2. The paclitaxel or docetaxel-polymer conjugate according to claim 1, wherein R1 is a (C1-C6) alkyl group; R2 is a (C2-C6) alkylene group; R3 is a (C1-C6) acyl group; t is an integer from 100 to 300; and d, e, f, g, h, i and j are each independently an integer from 0 to 100; provided that d+e is an integer from 1 to 100, and d+e+f+g+h+i+j is an integer from 6 to 100.

3. The paclitaxel or docetaxel-polymer conjugate according to claim 2, wherein R1 is a (C1-C3) alkyl group; R2 is a (C2-C4) alkylene group; R3 is a (C1-C3) acyl group; t is an integer from 100 to 300; and d, e, f, g, h, i and j each independently represent an integer from 0 to 90; provided that d+e is an integer from 1 to 90, and d+e+f+g+h+i+j is an integer from 15 to 90.

4. A paclitaxel or docetaxel-polymer conjugate, obtained by ester-bonding a carboxylic acid group of a block copolymer having a polyethylene glycol moiety and two or more amidated polyaspartic acid moieties to an alcoholic hydroxyl group of a paclitaxel or docetaxel, using a dehydrating condensing agent selected from the group consisting of dicyclohexylcarbodiimide, diisopropylcarbodiimide, 1-ethyl-3-(3-dimethylaminopropyl) carbodiimide hydrochloride and 1-ethoxycarbonyl-2-ethoxy-1,2-dihydroxyquinolinone in an organic solvent.

5. An anti-cancer agent comprising the paclitaxel or docetaxel-polymer conjugate according to any one of claims 1 to 3 and 4 as an active ingredient.

6. A method for producing the paclitaxel or docetaxel-polymer conjugate according to any one of claims 1 to 3, the method comprising ester-bonding a carboxylic acid group of a block copolymer having a polyethylene glycol moiety and two or more polyaspartic acid moieties to an alcoholic hydroxyl group of a paclitaxel or docetaxel, using a dehydrating condensing agent selected from the group consisting of dicyclohexylcarbodiimide, diisopropylcarbodiimide, 1-ethyl-3-(3-dimethylaminopropyl) carbodiimide hydrochloride and 1-ethoxycarbonyl-2-ethoxy-1,2-dihydroxyquinolinone in an organic solvent.

* * * * *